United States Patent [19]
McKinnie

[11] 4,294,775
[45] Oct. 13, 1981

[54] RESOLUTION OF ACYLATED D,L-ALKYL SUBSTITUTED ALKANOIC ACIDS

[75] Inventor: Bonnie G. McKinnie, Baton Rouge, La.

[73] Assignee: Ethyl Corporation, Richmond, Va.

[21] Appl. No.: 126,678

[22] Filed: Mar. 3, 1980

[51] Int. Cl.$^3$ .................. C07C 153/07; C07C 153/09
[52] U.S. Cl. .................................. 260/455 R; 562/401
[58] Field of Search .................... 562/401; 260/455 R; 560/103, 174

[56] References Cited
U.S. PATENT DOCUMENTS

| | | | |
|---|---|---|---|
| 3,665,032 | 5/1972 | Burch et al. | 562/401 |
| 3,796,748 | 3/1974 | Holdrege | 562/401 |
| 3,904,683 | 9/1975 | Day et al. | 562/401 |
| 4,046,889 | 9/1977 | Ondetti et al. | 424/244 |

OTHER PUBLICATIONS

Eliel, *Stereochemistry of Carbon Compounds*, pp. 49–52, McGraw-Hill, New York, N.Y., (1962).
Gottstein et al., *J. Org. Chem.*, 30, pp. 2072–2073, (1965).
Boyle, *Quarterly Reviews*, 25, pp. 323–326, (1971).
Wilen et al., *Tetrahedron*, 33, pp. 2725–2736, Pergamon Press, Great Britain, (1977).

*Primary Examiner*—Natalie Trousof
*Assistant Examiner*—Vera C. Clarke
*Attorney, Agent, or Firm*—Donald L. Johnson; John F. Sieberth; James M. Pelton

[57] ABSTRACT

A process for the resolution of racemic acyl-D,L-alkyl substituted alkanoic acids with an organoamine resolving agent, such as "Amine D," in a suitable solvent such as an alcohol or aqueous alcohol and recovery of the desired acylated D-alkyl substituted alkanoic acid.

12 Claims, No Drawings

RESOLUTION OF ACYLATED D,L-ALKYL SUBSTITUTED ALKANOIC ACIDS

BACKGROUND OF THE INVENTION

This invention relates to a process for resolution of racemic mixtures of substituted alkanoic acids. More specifically, the process of this invention relates to resolution of acylated D,L-alkyl substituted alkanoic acids useful as intermediates in the preparation of useful pharmaceutical products.

Resolution of racemic mixtures of optically active components was a problem faced by early chemists and is still with us today. Although significant progress continues to be made and new resolving agents and techniques are applied, it is still not today possible to carry out resolutions of organic compounds bearing functional groups quite rationally and with a high probability of success without the use of a systematic approach, a reasonably large collection of resolving agents and an understanding of phase and solubility behavior of stereoisomers to guide one during resolutions. Thus, occasionally the successful resolution of even simple organic compounds is difficult to achieve and in many cases such resolutions are often tedious. For this reason, many experienced investigators in the field of organic chemistry continue to view resolutions as an art, Wilen et al, *Tetrahedron*, Vol. 33, pp. 2725 et seq., Pergamon Press, Great Britain, 1977.

Of chief importance in the resolution of optically active enantiomers is the selection of a good resolving agent. The criteria involved include the following factors. (1) The compound between the resolving agent and the substance to be resolved should be easily formed and should also be easily broken up, for once one of the diastereoisomers is obtained in the pure state, it must be decomposed chemically so that the pure optically active material may be recovered. (2) The compound between the resolving agent and the substance to be resolved must be nicely crystalline, and there must be an appreciable difference in solubility between the compound formed by the resolving agent and the substance to be resolved. (3) The resolving agent must be either cheap or readily prepared or else readily and nearly quantitatively recoverable after completion of the resolution. If not, large scale resolutions become excessively tedious or expensive, Eliel, *Stereochemistry of Carbon Compounds*, pp. 49–51, McGraw-Hill, New York, N.Y. 1962.

In principle, all methods of resolution depend on one or the other of two facts: (1) that the products formed by the interaction of two enantiomers with a chiral reagent will be diastereomerically related and will therefore be susceptible to separation by conventional physical methods such as fractional crystallization, distillation, extraction, column chromatography or gas-liquid chromatography so that resolution is achieved if the desired enantiomers can be individually regenerated from the separated diastereomers, and (2) that enantiomers react at different rates with a chiral reagent so that when a pair of enantiomers interacts with a chiral reagent the transition states of the interaction are no longer mirror images of each other; thus, these transition states are diastereomeric rather than enantiomeric and will differ in, amongst other properties, internal energy. It follows that the activation energy for reaction of the enantiomers with a chiral reagent will be different and hence the difference in rates of reaction. Kinetic methods of resolution exploit this difference, Boyle, *Quarterly Reviews* 25, pp. 323–326, 1971.

The present invention takes advantage of the diastereomeric properties and seeks to separate the resultant diastereomers by crystallization.

DESCRIPTION OF THE INVENTION

This invention is based on the discovery that certain acyl alkanoic acids can be resolved by chiral resolving agents which are known but which heretofore have not been known to resolve the acylated D,L-alkyl substituted alkanoic acids described hereinbelow. Accordingly, it has been discovered that acylated 2-D,L-methyl carboxylic acids can be resolved with an organoamine resolving agent in a suitable solvent at temperatures sufficient to form the corresponding organoamine salts of the racemic acid mixture, cooling the resultant salt-containing solution at a rate to form the desired crystalline solid which precipitates from the solution, followed by separation of the desired crystalline solid, which is then washed and recrystallized and subsequently the desired optically active acyl carboxylic acid is recovered. More particularly, the present invention provides a process for resolving a racemic mixture of 3-acylthio-2-D,L-methylpropanoic acid by reacting such a racemic mixture of the acid with an organoamine resolving agent in a solvent suitable for the particular acid at a temperature sufficient to form the 3-acylthio-2-D,L-methylpropanoic acid organoamine salt, cooling the resultant salt-containing solution at a rate sufficient to preferentially form crystalline solids which are substantially enriched in the acylthio-2-D-methylpropanoic acid organoamine salt and separate said crystalline solids from the solution. A more highly preferred process of the present invention is provided by a process for resolving a racemic mixture of 3-benzoylthio- or 3-acetylthio-2-D,L-methylpropanoic acid comprising the steps of reacting said racemic mixture with an organoamine resolving agent in a suitable solvent at a temperature sufficient to form the 3-benzoylthio- or 3-acetylthio-2-D,L-methylpropanoic acid organoamine salt, cooling the resultant salt-containing solution at a rate sufficient to preferentially form crystalline solids containing a substantially enriched proportion of the 3-benzoylthio- or 3-acetylthio-2-D-methylpropanoic acid organoamine salt and precipitate said crystalline solids from the solution, separating said crystalline solids from the remaining salt-containing solution, solvent washing the crystalline solids and recrystallizing the washed salt followed by solvent washing at least two additional times to obtain a crystalline organoamine salt of 3-benzoylthio- or 3-acetylthio-2-D-methylpropanoic acid having less than about 3 mole percent of the L-enantiomer and work-up the recrystallized solid to spring the desired 3-benzoylthio- or 3-acetylthio-2-D-methylpropanoic acid and recovering the same from the acid solution.

The alkyl substituted carboxylic acids prepared by the present invention are useful as intermediates in the preparation of angiotensin converting enzyme inhibitors. This action is important since it has been discovered that inhibition of conversion of the decapeptide angiotensin I to angiotensin II is useful in reducing or relieving angiotensin related hypertension. The action of the enzyme renin on angiotensinogen, a pseudoglobulin in blood plasma produces angiotensin I. Angiotensin I is converted by angiotensin converting enzyme (ACE)

to angiotensin II. The latter is an active pressor substance present which has been implicated as the causative agent in various forms of hypertension in various mammalian species, e.g., rats and dogs. U.S. Pat. No. 4,046,889 teaches the use of certain proline derivatives such as azetidine-2-carboxylic acid derivatives are useful in reducing or relieving angiotensin related hypertension by inhibiting the conversion of angiotensin I and angiotensin II. Certain acylated 2-alkyl carboxylic acids are useful as intermediates to preparation of such azetidine-2-carboxylic acid derivatives described in U.S. Pat. No. 4,046,889, which is hereby incorporated by reference as if fully set forth. Particularly, the carboxylic acids which are propionic acids are specifically desirable. Further, the acyl group can be either an aroyl or an alkanoyl group. For example, benzoyl, p-toluoyl, formyl, acetyl and propanoyl are examples. Particularly preferred compounds of starting acids are acyl-thioalkanoic acids of the formula:

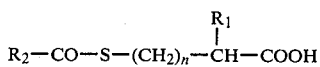

$$R_2-CO-S-(CH_2)_n-\underset{\underset{R_1}{|}}{C}H-COOH$$

in which $R_1$ is hydrogen or loweralkyl and $R_2$ is hydrogen, loweralkyl, phenyl or loweralkyl mono-substituted phenyl and n is 0, 1 or 2. Especially preferred acid starting materials are the racemates 3-benzoylthio-2-D,L-methylpropanoic acid and 3-acetylthio-2-D,L-methylpropanoic acid.

The above acids have been found to be readily resolved by an organoamine resolution agent, such as an abiethylamine. Quite unexpectedly, it was found that an organoamine resolution agent known commercially as "Amine D" successfully resolved the acylthio alkanoic acids of the above formula. "Amine D," formerly "Rosin Amine D," is a tradename of the Hercules Powder Company and is believed to be composed of an average of 50% dehydroabietylamine, 20% dihydroabietylamine, 20% tetrahydroabietylamine and 10% inert rosin, Note 3, Gottstein and Cheney, J. Organic Chem., 30, p. 2072, (1965). The "Amine D" is a clear, yellow, viscous liquid with a neutralization equivalent of 316. Upon reaction with the racemic acylthio carboxylic acid, a solid salt is formed.

The reaction of the resolving agent and the acid takes place in a solvent in which the resultant salt is sufficiently soluble.

Ideally, the solvent should be one from which the desired diastereomeric compound can be precipitated without the undesired diastereomeric compound also crystallizing and precipitating. It has been found that solvents having active oxygens such as alcohols, ketones, and aldehydes and such solvents containing small amounts of water meet this criteria. Typical of such solvents are alcohols, esters, ketones and aldehydes. Examples of such solvents are ethanol, propanol, isopropanol, butanol, acetone, methyl ethyl ketone and azeotropic mixtures of such solvents. Especially preferred is isopropanol and aqueous mixtures of isopropanol and a most preferred solvent is an azeotropic isopropanol-water mixture containing about 88% isopropanol on a weight basis.

The reaction of the acid and resolving agent in the solvent can take place at any temperature high enough to give good reaction rates without degradation of reactants or low enough to be susceptible of good yields and without causing crystallization prematurely. Thus, temperatures from about 0° up to 100° C. can be employed for the reaction of the racemic mixture of the acylthio alkanoic acid and the organoamine resolving agent. After a sufficient time for completion of the formation of the resultant salt, the reaction mixture is cooled to the point of crystallization of the desired D-diastereomer salt.

Since too fast a rate of cooling will also cause crystallization and precipitation of the undesired L-diastereomeric salt, it is important that the cooling rate be sufficient to allow crystallization and precipitation of only the desired acyl-D-alkanoic acid salt. Usually, cooling rates which give optimum precipitation of the desired salt are found by trial and error in the present invention. It has also been found that cooling too fast leads to solidification of the suspension. For example, a cooling at a rate of 25° to 30° C. per hour from about 65° C. leads to solidification of the mixture. Thus, a cooling rate of sufficient rapidity to give optimum results must be determined for each solvent and each salt. It has been found that when the solution is cooled more slowly such as, for example, at a rate of not more than about 20° C. per hour from about 65° C. to about 45° C. in the case of 3-benzoylthio-2-methylpropanoic acid "Amine D" salt, the best results are obtained. Without limiting the invention unduly, it should be noted that the optimum cooling rate for the present process must be determined for each salt so that optimum yields and reactor productivity can be achieved.

Upon separation of the precipitated "Amine D" acylthio-2-D-carboxylic acid salt from the remaining solvent, it will be noted that additional desired products still remain in the solvent and further some of the undesired L-diastereomeric salt will also have been precipitated. Thus, it can be easily appreciated that recrystallization will be useful to further increase purification of the desired D-diastereomeric salt. It has been found that at least three crystallizations, i.e., the original crystallization and two crystallizations, are preferred in order to obtain the desired D-optical enantiomeric salt in optical purities of greater than 96%. Thus, it is advantageous to recrystallize at least twice and to seed the cooling solution with crystals of the desired product. Moreover, one skilled in the art will certainly recognize that additional product can be obtained if the filtrate from the crystallization is recycled to carry out further separations of additional batches of the diastereomeric mixture.

Once the desired acylthio-2-D-carboxylic acid "Amine D" salt is obtained, the acid can be recovered and the "Amine D" discarded. A typical work-up procedure involves basification by addition to the aqueous slurry of salt of sodium carbonate and caustic, extraction of the resultant mixture with a suitable solvent, such as cyclohexane, acidification of the aqueous layer, followed by one or more solvent extractions, as before with cyclohexane, for example, drying by azeotropic distillation and crystallization to obtain practically pure solid acylthio-D-carboxylic acid.

The following examples are used to illustrate but not limit the process of the present invention.

EXAMPLE 1

Resolution of 3-benzoylthio-2-D,L-methylpropanoic acid

In a suitable reaction flask, 43 grams (42.3 ml) of methacrylic acid was added dropwise to 74 grams (63.0 ml) of thiobenzoic acid which was preheated to 80° C.

The addition took place over 30 minutes and the temperature rose to 97°–105° C. After addition of the methacrylic acid was complete, the reaction mixture was maintained at 95° to 100° C. for an additional 20 minutes. Analysis of a sample of the reaction mixture indicated that 6% of the methacrylic acid was still present. Heating was continued another 20 minutes and the reaction mixture was then taken up in 88% by weight isopropanol-water mixture. Then there was added 174 grams of "Amine D" dissolved in 88% by weight isopropanol-water. The solution at 40° C. was then diluted to 1450 ml with the isopropanol-water solvent and cooled slowly to 20° C. over a period of 30 minutes. After 20 minutes at 20° C. with continued stirring, the solid was collected in a Buchner funnel and washed with 200 ml of cold isopropanol. The combined wash and filtrate totaled 1300 ml and there was obtained 215 grams of a wet filter cake identified as Sample 1A. A small portion of Sample 1A was taken and oven dried at 90° C. and lost 49% of its weight. The remainder of Sample 1A was diluted to 1000 ml with 88% isopropanol-water and brought to a boil to dissolve the solids. Upon cooling to room temperature slowly, a precipitate was formed and collected in a Buchner funnel. The precipitate was washed with 150 ml of cold 88% isopropanol-water and identified as Sample 1B, weight 191.2 grams. A small portion of Sample 1B lost 56% of its weight upon oven drying. Optical rotations were taken of Samples 1A and 1B on a Perkins-Elmer Model 141 polarimeter using a 1 dm cell holding 5 ml. Solutions for rotations were prepared in 10 ml volumetric flasks. Sample 1A had $[\alpha]^{20}_D = +5.16°$ (c=3.68, CHCl$_3$) and Sample 1B had $[\alpha]^{20}_D = -1.0°$ (c=3.358, CHCl$_3$).

The wet filter cake from Sample 1B was diluted to 700 ml with 88% isopropanol-water and heated to boiling, dissolving all solids. An additional amount of 88% isopropanol-water was added to make 1320 ml. The mixture was then cooled, giving a precipitate which was collected by filtering in a Buchner funnel, and the wet filter cake was washed with 150 ml of isopropanol and identified as Sample 1C, weighing 134.3 grams with about 49.7% loss on drying.

Sample 1C was diluted to 400 ml with water and 3 grams of sodium carbonate were added with 4.77 grams of sodium hydroxide in 30 ml of water in small portions. Most of the solid dissolved. An additional 4 grams of sodium carbonte was added and the solution was heated until all solid dissolved. The warm solution was extracted twice with cyclohexane and then the aqueous layer was acidified with 21 ml of concentrated hydrochloric acid. A second series of two extractions at 60° C. was undertaken with a total of 200 ml of cyclohexane. The cyclohexane solution was washed with 150 ml of water, then evaporated to 120 ml and cooled to room temperature overnight. The next day, the cyclohexane solution had no solids precipitated, but on seeding with crystals there was a rapid deposition of solid crystals. The crystals from cyclohexane solution were collected by a Buchner funnel from the cyclohexane to give 23.51 grams of 3-benzoyl-2-D-methylpropanoic acid having optical rotation of $[\alpha]^{20}_D = -43.81°$ (c=7.874, 3 A ethanol).

Yields from the crystallizations amounted to 86% of Somple 1A, 66% of Sample 1B and 53% of Sample 1C as the "Amine D" salt.

EXAMPLE 2

Recycle of solvents in the resolution of the racemic mixtures of Example 1 is illustrated in the following example.

To 134 grams (114 ml) of thiobenzoic acid heated at 80° was added 77 grams (76 ml) of methacrylic acid over 30 minutes by dropwise addition, while the temperature was maintained between 97° and 105° C. After addition was complete, heating was continued for 40 minutes at 95° to 100° C. The resulting racemic mixture of 3-benzoyl-2-D,L-methylpropionic acid was dissolved in the filtrate separated from Sample 1B, warmed and 305 grams of "Amine D" were added. The resultant mixture was diluted with 88% isopropanol to 1650 ml. At 50° C., the solution gave a precipitate. Then the solution was cooled to 25° C., filtered through a Buchner funnel, and washed on the Buchner with an additional 300 ml of isopropanol giving 431.3 grams of wet filter cake and 1400 ml of filtrate plus wash material. The sample was identified as 2A. Optical rotation of Sample 2A had $[\alpha]^{20}_D = +6.83°$ (c=1.83, CHCl$_3$). Sample 2A was then diluted to 1600 ml with the filtrate removed from Sample 1C and brought to a boil dissolving all solids. An additional 250 ml of filtrate from Sample 1C was added to the reaction mixture. This solution was cooled to 20° C., the solid precipitate was filtered and washed with an additional 250 ml of 88% isopropanol-water giving 305.6 grams of wet filter cake, identified as Sample 2B. A small portion was dried in the oven and lost 48% of its weight on drying. There was 1580 ml of filtrate and wash from Sample 2B. Sample 2B was reslurried in fresh 88% isopropanol-water, 1700 ml total volume, brought to a boil to dissolve all solids, then cooled to 20° C. slowly. The crystals were collected and the filter cake was washed with an additional 200 ml of isopropanol to give 283 grams of wet filter cake and 1520 ml of filtrate plus wash. The filter cake was identified as Sample 2C and its optical rotation was determined to be $[\alpha]^{20}_D = -3.10°$ (c=3.86, CHCl$_3$). The loss on drying a small portion was determined to be 49% and a 63% yield as the "Amine D" salt was calculated.

280 Grams of Sample 2C was diluted with 450 ml of water to give a thick paste. To the paste was added 4.5 grams of sodium carbonate followed by dropwise addition over 15 minutes of a solution of 10.18 grams of sodium hydroxide in 50 ml of water. All solids were dissolved. The solution was heated to 45° C. and extracted twice with cyclohexane to recover the "Amine D." The aqueous solution was then acidified with 30 ml of concentrated hydrochloric acid and again extracted twice with about 175 ml each of cyclohexane. The combined extracts were washed with 100 ml of water at 50° C. and the 410 ml cyclohexane solution was boiled down to 220 ml. On cooling, 40.8 grams of 3-benzoylthio-2-D-methylpropanoic acid was recovered by filtration on a Buchner funnel. The filtrate was again concentrated to 50 ml and on cooling gave a second crop of the product weighing 14.38 grams after filtration.

Optical rotations of the first and second crystal crops, respectively, are $[\alpha]^{20}_D = -43.51°$ (c=4.532, 3 A ethanol), optical purity, 98.6% and $[\alpha]^{20}_D = -41.99°$ (c=3.746, 3 A ethanol), and optical purity, 95%. Yield of desired product from Sample 2C was 88%.

EXAMPLE 3

In a manner similar to Example 1, 3-benzoyl-2-D,L-methylpropanoic acid was prepared and resolved according to the following procedure. To 134 grams (0.97 mols) of thiobenzoic acid heated to 80° C. was added dropwise over one-half hour 77 grams (0.895 mols) of methacrylic acid. The temperature was kept under 110°. After heating one hour following the completion of addition at 95°–100° C., the analysis of the sample showed about 2.5 mol percent methacrylic acid still present. The resulting racemic acid was taken up in 900 ml of the filtrate from Sample 2B and warmed to 40° C. Then 301 grams of "Amine D" was dissolved at 40° C. in 1800 ml of the filtrate from Sample 2B and added to the racemic acid filtrate solution. The temperature rose to 50° C. The hot solution was seeded with crystals of 3-benzoyl-2-D-methylpropanoic acid "Amine D" salt and cooled to 20° C. over 30 minutes using manual stirring. After 15 minutes at 20° C., the viscous malt-like slurry was filtered and the crystals pressed dry using a rubber dam. They were then washed with 300 ml of 88% isopropanol-water solution and again pressed dry leaving 560 grams of wet cake which is identified as Sample 3A. A small portion of Sample 3A lost 55 percent of its weight on oven drying. The dried salt had an optical rotation of $[\alpha]^{20}_D = +8.05°$ (c=4.72, CHCl$_3$).

The wet cake Sample 3A was taken up in 1300 ml of the filtrate of Sample 2C and brought to a boil to dissolve all solids. This solution was cooled to about 65° C., seeded with salt crystals as above, then cooled to 20° C. over 30 minutes with stirring. The crystals were collected by filtration in a Buchner funnel and washed with 250 ml of 88% isopropanol-water giving 1650 ml of filtrate and wash. The crystals were identified as Sample 3B and the wet filter cake weighed 426 grams. A portion of Sample 3B lost 55 percent of its weight on drying and had an optical rotation of $[\alpha]^{20}_D = +0.3°$ (c=3.6, CHCl$_3$).

Sample 3B was crystallized from fresh 88% isopropanol-water, total volume 1800 ml, and the crystals were identified as Sample 3C. The wet filter cake weighted 290 grams and lost about 54 percent of its weight on drying. The yield of the "Amine D" salt from resolution was about 70%. Sample 3C had optical rotation of $[\alpha]^{20}_D = -2.5°$ (c=4.164, CHCl$_3$).

EXAMPLE 4

This example illustrates the preparation and resolution of 3-acetylthio-2-D,L-methylpropanoic acid.

To 40 ml of thioacetic acid (about 85 percent) was added dropwise at 95°–115° C. about 39.3 ml of methacrylic acid. After one hour reaction at 95°–105° C., only a trace of methacrylic acid was present as shown by NMR analysis. The reaction mixture was then stripped of acetic acid.

To a solution of 150 grams of 3-acetylthio-2-D,L-methylpropanoic acid, prepared as above, in isopropanol was added 292 grams of "Amine D," also in isopropanol. This reaction mixture at 31° C. was diluted to 1500 ml with isopropanol. The reaction mixture was seeded with crystals of 3-acetylthio-2-D-methylpropanoic acid "Amine D" salt and cooled with precipitation beginning at about 22° C. Cooling continued until 18° C. at which time stirring stopped. The reaction mixture was further cooled over about 30 minutes with occasional manual stirring to 2° C., and the thick slurry was then filtered and washed with 160 ml of cold isopropanol. The wet cake, identified as Sample 4A, weighed 409 grams and was taken up in isopropanol, heated to 46° C., and diluted to 1575 ml to dissolve all solids. It was then cooled to 25° C., seeded with crystals of 3-acetylthio-2-D-methylpropanoic acid "Amine D" salt, cooled to 22° C. and held at that temperature ten minutes with the reaction mixture nearly solidifying. It was then further cooled in an ice bath with stirring to 2° C. over a 45 minute period. After filtration, the sample was washed with 160 ml of isopropanol and identified as Sample 4B.

Following the above procedure, Sample 4B was again crystallized after dissolving in isopropanol at a total reaction volume of 1575 ml, cooled, seeded, filtered and washed with 100 ml of isopropanol to give 287 grams of wet cake, identified as Sample 4C. Sample 4C had optical rotation of $[\alpha]^{20}_D = +8.06°$ (c=1.5, 3 A ethanol). Sample 4C was hydrolyzed by reacting with sodium carbonate in water and ether. The gel formed was broken by addition of methylene chloride and acetone. The aqueous layer was separated, washed with additional methylene chloride, acidified with sulfuric acid and extracted twice with methylene chloride. The aqueous layer was dried over magnesium sulfate, concentrated and distilled to give three cuts, Cut 1 being 2.65 grams, boiling point 89° at 0.1 mm mercury; Cut 2, 3.56 grams, boiling point 89°–99° C. at 0.1 mm mercury and Cut 3, 11.76 grams, boiling point 99°–103°0 C. at 0.1 mm mercury. The optical rotations of Cuts 2 and 3 are $[\alpha]^{20}_D = -35.60°$ (c=3.952, 3 A ethanol) and $[\alpha]^{20}_D = -35.80°$ (c=3.578, 3 A ethanol), respectively. The yield of the resolved acid product cuts, based on starting racemic mixture, was 46 percent.

EXAMPLE 5

The filtrate from Sample 4B was employed as the reaction solvent in the resolution of 3-acetylthio-2-D,L-methylpropanoic acid as illustrated in this example. To 1400 ml of the filtrate from Sample 4B was added 150 grams of 3-acetylthio-2-D,L-methylpropanoic acid, prepared as in Example 4. Also, 292 grams of "Amine D" were added. Crystallization of this mixture, 1820 ml total reaction mixture volume, according to the procedures of Example 4, gave a wet filter cake identified as Sample 5A which was washed with 150 ml of isopropanol. The washed filter cake weighed 444 grams wet and a portion of Sample 5A lost about 47 percent of its weight on drying. Sample 5A was taken up in 1200 ml of the filtrate from Sample 4C, total 1800 ml reaction mixture heated to 45° C. and 150 ml of isopropanol was added to dissolve all the solids. This solution was crystallized at 2° C. as indicated in Example 4 to give a wet filter cake identified as Sample 5B, which was washed with 150 ml of isopropanol. Sample 5B wet filter cake had about 48 percent by weight of solvent.

Sample 5B was in a similar manner crystallized from fresh isopropanol, total volume 1600 ml, washed with an additional 150 ml giving 268 grams of wet filter cake identified as Sample 5C, a portion of which lost 39 percent on drying. Sample 5C had optical rotation of $[\alpha]^{20}_D = +7.92°$ (c=1.995, 3 A ethanol). Sample 5C was recrystallized a fourth time, this time using 1400 ml of isopropanol and washing with 100 ml to give 136.5 grams of wet filter cake identified as Sample 5D. A portion of Sample 5D lost 45% on drying. The optical rotation of Sample 5D was $[\alpha]^{20}_D = +5.7°$ (c=1.585, 3 A ethanol). Hydrolysis of Sample 5D with 19 grams of sodium carbonate and extraction with cyclohexane gave a gel which was broken with methylene chloride. Acidification and work-up with methylene chloride gave a liquid which was distilled through a 7 cm Vigreux column giving, after a forecut, 21.33 grams of liquid 3-acetylthio-2-D-methylpropanoic acid boiling at 97°-107° C. at 0.4 mm mercury and having optical rotation of $[\alpha]^{20}_D = -40.76°$ (c=5.23, 3 A ethanol). The crystallization yield of Sample 5D from the racemic acid was 36.4 percent.

EXAMPLE 6

This example illustrates the preparation of 3-p-toluoylthio-2-D,L-methylpropanoic acid and its resolution by the process of the present invention.

To 37.2 g of crude thio-p-toluic acid was added 21 ml of methacrylic acid. This was heated for 1 hour at 100°-110° C., then cooled and crystallized from cyclohexane. It was taken up again in cyclohexane and cooled slowly forming solid 3-p-toluoylthio-2-D,L-methylpropanoic acid which after recrystallization twice from cyclohexane had a melting point of 84°-86° C.

Then 10 grams of this solid was dissolved in 50 ml of 88 wt. percent isopropanol-water and added to a solution of 13.2 grams of "Amine D" in 50 mls of warm 88 wt. percent isopropanol-water mixture. The solution cooled to room temperature and after one-half hour the resultant solid was filtered and the filter cake was washed with 15 ml of 88 wt. percent isopropanol-water. The cake was dissolved in 110 ml of 88 wt. percent isopropanol-water at 78° C., cooled slowly to room temperature and, after one-half hour, filtered. The filter cake was redissolved in 110 ml hot 88 wt. percent isopropanol-water, the mixture was cooled slowly to room temperature and allowed to stand for one-half hour. The mixture was filtered, washed with 15 ml of 88 wt. percent isopropanol-water and the solid was dried under vacuum leaving a white solid resolved-acid-"Amine D" salt. The resolved acid-"Amine D" salt was taken up in aqueous $Na_2CO_3$, then extracted twice with methylene chloride-diethyl ether to remove the liberated "Amine D." The resultant aqueous solution was acidified with concentrated hydrochloric acid and extracted with methylene chloride. The extract was dried over magnesium sulfate, the methylene chloride was stripped off and the resultant solid crystallized from cyclohexane. The precipitate was collected, washed with cyclohexane and dried. The resolved acid had an optical rotation of $[\alpha]^{20}_D = -36.3°$ (c=2.15, 3 A ethanol).

EXAMPLE 7

This example illustrates the preparation of 3-propanoylthio-2-D,L-methylpropanoic acid and its resolution.

To 70 ml of thiopropanoic acid heated at 90° C. was added dropwise 60 ml of methacrylic acid over a one-half hour period while maintaining the temperature at 90°-120° C. The reaction mixture was heated for an additional 1 hour at 100° C. and then cooled slowly to room temperature. The product was distilled and after a forecut, 105 g of 3-propanoylthio-2-D,L-methylpropanoic acid, a bright yellow liquid, b.p. 110°-114° C. at 10.4 mm Hg, was obtained. Analysis was confirmed by NMR.

Resolution was carried out by dissolving 40 grams of the above product in 150 ml of isopropanol at 27° C. and adding to 71.6 grams of "Amine D" in 150 ml of isopropanol. The temperature rose to 42° C. The reaction mixture was cooled to 5° C. at which time crystallization occurred. The cooled mixture was filtered, the filter cake diluted to 300 ml with isopropanol, heated to 50° C. to dissolve all solids and cooled to 2°-5° C. to crystallize. The solid precipitant was filtered and washed with 50 ml of cold isopropanol and recrystallized again from 200 ml of isopropanol at 50° C. cooled to 2°-5° C. The resultant solid, after washing with isopropanol gave 29.5 g of wet resolved acid-"Amine D" salt filter cake.

The salt was taken up in water and excess sodium carbonate added, the resultant mixture extracted twice with methylene chloride and then the aqueous phase acidified with hydrochloric acid. Extraction with methylene chloride, drying and evaporation of the solvent left a clear colorless liquid. Simple distillation of the liquid gave a resolved acid product, b.p. 110° C. at 0.1 mm Hg having optical rotation of $[\alpha]^{20}_D = -40.89°$ (c=3.167, 3 A ethanol).

From the above illustrative examples, it is clear that various schemes can be envisioned for use and recycle of the crystallization solvent. It should be noted, however, that solvent recycle is carried out for practicality and economical advantage and it is not required to recycle filtrates obtained from crystallization in order to practice the present process. It should also be clear from the illustrative examples that the organoamine resolving agent has sufficient resolution ability to selectively precipitate the desired D-enantiomer from solution. The examples further illustrate the ease with which the resolving agent can be removed from the desired D optical enantiomer of the acid. Accordingly, having disclosed the process of the present invention, one skilled in the art would be aware of changes and variations which could be employed within the scope and spirit of the invention. Therefore, it is desired that the invention be limited only by the lawful scope of the following claims.

What is claimed is:

1. A process for resolving a racemic mixture of 3-benzoylthio- or 3-acetylthio-2-D,L-methylpropanoic acid comprising the steps of reacting said racemic mixture with an organoamine resolving agent in a solvent having an active oxygen selected from alcohols, ketones, esters and aldehydes suitable for the particular acid at a temperature sufficient to form the 3-benzoylthio- or 3-acetylthio-2-D,L-methylpropanoic acid organo-amine salt, cooling the resultant salt-containing solution at a rate sufficient to preferentially form crystalline solids containing a substantially enriched proportion of the 3-benzoylthio- or 3-acetylthio-2-D-methylpropanoic acid organoamine salt and separating said crystalline solids from the remaining salt-containing solution and recovering from the resultant crystalline solids said 3-benzoylthio- or 3-acetylthio-2-D-methylpropanoic acid.

2. The process of claim 1 in which the racemic mixture is 3-benzoylthio-2-D,L-methylpropanoic acid which is resolved to obtain 3-benzoylthio-2-D-methylpropanoic acid.

3. The process of claim 1 in which the racemic mixture is 3-acetylthio-2-D,L-methylpropanoic acid which is resolved to obtain 3-acetylthio-2-D-methylpropanoic acid.

4. The process of claim 1 wherein said solvent comprises isopropanol.

5. The process of claim 2 wherein said solvent is an aqueous mixture of isopropanol.

6. The process of claim 5 wherein said solvent is an azeotropic isopropanol-water mixture.

7. The process of claim 3 wherein said solvent is isopropanol substantially free of water.

8. The process of claim 1 wherein said organoamine resolving agent is an abietylamine.

9. The process of claim 1 wherein said organoamine resolving agent is a mixture of abietylamines.

10. The process of claim 1 wherein said organoamine resolving agent is a mixture of dehydroabietylamine, dihydroabietylamine and tetrahydroabietylamine.

11. The process of claim 2 wherein said reacting is carried out at a temperature between about 40° C. and the boiling point of the solvent and the cooling is carried out at from the reaction temperature to about 20° C.

12. The process of claim 3 wherein said reacting is carried out at a temperature between about 20° to about 50° C. and the cooling is carried out at from the reaction temperature to about 0° C.

* * * * *